US00PP35326P2

(12) United States Plant Patent
Kappel

(10) Patent No.: US PP35,326 P2
(45) Date of Patent: Aug. 22, 2023

(54) ***PRUNUS* PLANT NAMED 'SPC414'**

(50) Latin Name: *Prunus avium*
Varietal Denomination: SPC414

(71) Applicant: Her Majesty the Queen in Right of Canada as Represented by the Minister of Agriculture and Agri-Food, Ottawa (CA)

(72) Inventor: Frank Kappel, Kanata (CA)

(73) Assignee: HER MAJESTY THE QUEEN IN RIGHT OF CANADA AS REPRESENTED BY THE MINISTER OF AGRICULTURE AND AGRI-FOOD, Ottawa (CA)

( * ) Notice: Subject to any disclaimer, the term of this patent is extended or adjusted under 35 U.S.C. 154(b) by 0 days.

(21) Appl. No.: 17/953,100

(22) Filed: Sep. 26, 2022

Related U.S. Application Data

(60) Provisional application No. 63/248,729, filed on Sep. 27, 2021.

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 6/7445; A01H 5/08
See application file for complete search history.

*Primary Examiner* — Keith O. Robinson
(74) *Attorney, Agent, or Firm* — Penny J. Aguirre

(57) ABSTRACT

A new cultivar of *Prunus avium* tree named 'SPC414' that is characterized by its mid-season fruit harvest, its fruit that is large and very firm with a desirable appearance, its fruit with a low level of natural splitting, its flowers that are self-fertile, its fruit with good storage potential in regular air MAP bag, and its slight nose dimple on the calyx at the end of the fruit.

1 Drawing Sheet

Botanical classification: *Prunus avium.*
Variety denomination: 'SPC414'.

BACKGROUND OF THE INVENTION

The present invention relates to a new and distinct cultivar of *Prunus avium* and will be referred to hereafter by its cultivar name, 'SPC414'. 'SPC414' is a new cultivar of sweet cherry tree grown for fruit production.

The new cultivar of *Prunus* arose from a breeding program conducted by the Inventor at a research center in Summerland, B.C., Canada with the goal of developing a new cultivar of cherry tree with improved fruit appearance, taste, firmness, flesh texture, productivity, precocity, harvest timing, and split resistance with improved tree quality and disease resistance.

The new cultivar arose from open pollination of 'Lapins' (not patented) in 1996. The male parent is therefore unknown. The Inventor selected 'SPC414' as a single unique plant amongst the resulting seedlings in 2002.

Asexual propagation of the new cultivar was first accomplished by budding onto Mazzard rootstock (not patented) by the Inventor in Summerland, B.C., Canada in 2004. Asexual propagation by budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SPC414' as a unique cultivar of cherry tree.

1. 'SPC414' exhibits a mid-season fruit harvest.
2. 'SPC414' exhibits fruit that is large and very firm with a desirable appearance.
3. 'SPC414' exhibits fruit with a low level of natural splitting.
4. 'SPC414' exhibits flowers that are self-fertile.
5. 'SPC414' exhibits fruit with good storage potential in regular air MAP (Modified Atmosphere packaging) bag.
6. 'SPC414' exhibits a slight nose dimple on the calyx at the end of the fruit.

The female parent, 'Lapins', differs from 'SPC414' in having a later harvest time and fruit that are smaller and less firm. 'SPC414' can be most closely compared to the cultivars 'Bing' (not patented) and 'SPC342' (U.S. Plant Pat. No. 29,788). 'Bing' is similar to 'SPC414' in having a mid-season harvest time and dark red cherries. 'Bing' differs from 'SPC414' in having fruits that are much smaller in size, flowers that are not self-fertile with an earlier bloom period. 'SPC342' is similar to 'SPC414' in having large sized fruit with excellent eating attributes and a mid-season harvest time. 'SPC342' differs from 'SPC414' in having larger fruit, flowers that are not self-fertile, more moderate fruit productive on Mazzard rootstock, and leaves that develop small red dots at harvest.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure included but may not be limited to a website listing by ANFIC Fruit Variety Catalogue (as a trial variety).

BRIEF DESCRIPTION OF THE DRAWING

The accompanying color photograph illustrates the overall appearance and distinct characteristics of the fruit of 'SPC414' on a 17-year-old tree as grown in a trial plot in Summerland, B.C., Canada. The photograph provides a view of a cluster of fruit of 'SPC414'. The colors in the photograph are as close as possible with the digital photography techniques available, the color values cited in the detailed botanical description accurately describe the colors of the cherry tree.

DETAILED BOTANICAL DESCRIPTION

The following is a detailed description of 17-year-old trees as grown in a trial plot in Summerland, B.C., Canada. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

General description:

*Plant type*.—Deciduous fruit bearing tree.

*Plant habit*.—Upright and spreading with medium crown density.

*Height and spread*.—Reaches about 4 m in height and about 2.4 m in spread when grown on Mazzard rootstock in a 2.4 m by 4.5 m training pattern.

*Cold hardiness*.—To at least U.S.D.A. Zone 6.

*Diseases and pests*.—No susceptibility or resistance to diseases or pests has been observed.

*Root description*.—Fibrous, freely branched.

*Propagation*.—Budding onto Mazzard rootstock.

*Growth rate*.—Moderate to vigorous.

Trunk description:

*Size of trunk*.—23 cm in diameter measured 30 cm above soil level.

*Bark color*.—187A, older bark 198B.

*Bark texture*.—Young stems; smooth with horizontal lenticels 187A in color, older bark; rougher textured.

*Tree branching*.—Medium.

Description of dormant shoots (one year-old):

*Pubescence*.—None.

*Shoot size*.—Average of 81.6 cm in length and 1.18 cm in width at basal end.

*Anthocyanin presence*.—None.

*Thickness of shoot at center of middle internode*.—Medium; average of 7.3 mm.

*Bark color*.—165A, lenticels 163D, larger branches can have short longitudinal striations of 188D.

*Shoot angle*.—Erect.

*Lenticels*.—7 per square cm.

*Branch internode length*.—Average of 4.2 cm.

*Vegetative buds*.—Large in size; 4.9 mm in length and 3.6 mm width, conical to round in shape, adpressed and held slightly out from shoot, support is medium.

Description of growing shoots:

*Color of growing tip of shoot*.—144B.

*Pubescence of shoots tip*.—None.

*Anthocyanin presence*.—None.

Foliage description:

*Leaf shape*.—Elliptical.

*Leaf division*.—Simple.

*Leaf base*.—Generally rounded with some cordate and acute.

*Leaf apex*.—Acuminate at very tip.

*Leaf fragrance*.—None.

*Leaf burst*.—Early in the beginning of full flowering.

*Leaf venation*.—Pinnate, not prominent, color; upper surface matches leaf color except midrib 145C, lower surface 145C with light streaks of 187A.

*Leaf margins*.—Biserrate.

*Leaf arrangement*.—Alternate.

*Leaf aspect*.—Slightly concave and held horizontal to oblique downward in relation to shoot.

*Leaf attachment*.—Petiolate.

*Leaf surface*.—Glabrous and slightly glossy on upper surface and weakly to moderately pubescent on lower surface.

*Leaf size*.—Mature leaves average 17.3 cm in length and 8.4 cm in width.

*Leaf internodes*.—Average of 6 cm.

*Leaf color*.—Newly expanded leaves upper and lower surface; 174B with 139C around the spine, veins, and serration tips, mature leaves upper and lower surface; 137B to 137A.

*Petioles*.—Average of 3.4 cm in length and 1.8 mm in width, color; front of petiole 187A in color with back of petiole 145B with anthocyanins 187A, glabrous surface.

Inflorescence description:

*Blooming period*.—Mid-late; relative to sweet cherry bloom season in Summerland BC, Canada.

*Inflorescence type*.—Clusters of single flowers.

*Lastingness of inflorescence*.-An average of 5 days.

*Flower fragrance*.—Very slight vegetative/floral scent.

*Flower quantity*.—Average of 2 to 3 per inflorescence.

*Flower type*.—Rotate corolla above an elongated calyx with stamens and pistil extended.

*Flower size*.—Average of 3.7 cm in diameter.

*Calyx*.—Comprised of sepals fused into an ovoid base with un-fused portions spreading at apex.

*Sepals*.—5, 146D in color, glabrous surface, 6.9 mm in length with un-fused portions about 4.8 mm in width, entire glandular margin, attenuate apex, fused base.

*Petals*.—5, broadly elliptic in shape, un-fused, thin and papery substance, smooth margin, rounded base, emarginate apex, about 1.65 cm in length and 1.34 cm in width, both surfaces 155D in color.

*Pedicels*.—Average of 1.6 cm in length, 1.4 mm in width, 146D in color, glabrous surface.

*Rachis*.—Glabrous surface, flowers lightly compacted with whorled arrangement.

*Nectaries*.—Present.

Reproductive organs:

*Gynoecium*.—Pistil; 1, about 1.7 cm in length and extending beyond perianth, style; 150C in color, style and stigma together; 1.43 cm in length, stigma; <1 mm in diameter, 153B in color, ovary is superior, glabrous, 144B in color, nectarines; 2, kidney shaped, 46B in color.

*Androecium*.—Stamens; 35, base adnate to calyx, filaments; 155D in color, 13.4 mm in length and <1 mm in width, anthers; 163A in color, dorsifixed, 1.4 mm in length and <1 mm in width, pollen; abundant in quantity, 163B in color.

*Fertility*.—Self-fertile.

Fruit description:

*Fruit type*.—Drupe.

*Fruit shape*.—Kidney to reniform.

*Fruit apex*.—Flat with slight concave depressed apex, moderate-low susceptibility to rain induced cracking.

*Fruit size*.—Large, 3.0 cm in length and 2.6 cm in width.

*Fruit firmness*.—Firm.

*Fruit set*.—Medium-high.

*Fruit stalk*.—Long and medium in thickness; 5.1 cm in length and 1.2 mm in width, surface fine with vertical striations, color 145A.

*Fruit bearing*.—Intermediate precocity.

*No. of fruit per cluster*.—Typically 2.

*Skin color*.—Between 202A and 187A, when ripe covered with light colored dots.

*Harvest date*.—Mid-season; average of July 7th in Summerland, BC, Canada.

*Skin surface*.—Glossy and glabrous.

*Skin suture*.—Moderate prominence.

*Flesh color*.—187B.

*Juice*.—Moderate juiciness, 187A in color.

*Flesh texture*.—Fleshy, moderately juicy.

*Apex scar*.—Size medium; an average of 1 mm in diameter, 166D in color.

*Flavor*.—Medium sweetness.

*Fruit use*.—Fresh Fruit.

*Weight*.—11.5 g.

*Brix*.—19.3%.

*Acidity*.—11.6 TA (ml of NaOH).

*Storage life*.—Up to +6 weeks at 1° C.).

*Seeds*.—1 stone per berry, 164D in color, medium in size; average of 1.12 cm in length and 1.07 cm in width and medium in comparison to fruit, shape; lateral view is symmetrical, slight semi-adherence to flesh, front view is broadly elliptic, basal view is round, keel is strongly developed.

It is claimed:

1. A new and distinct cultivar of *Prunus* tree named 'SPC414' as herein illustrated and described.

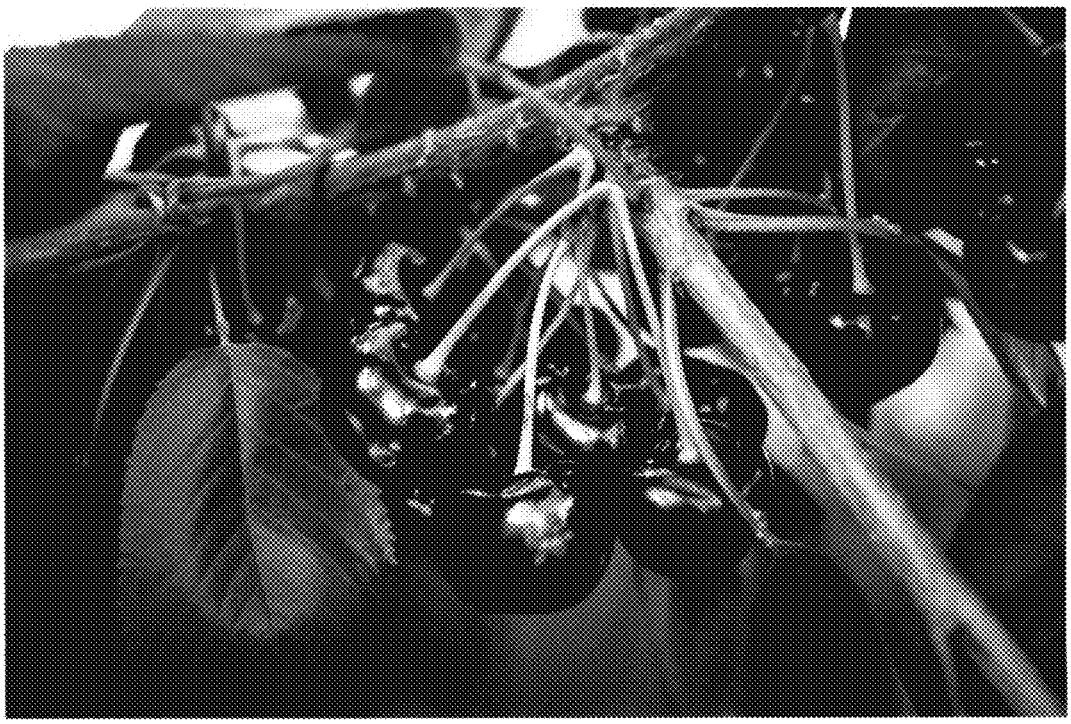

* * * * *